United States Patent
Nagase et al.

(10) Patent No.: US 9,983,051 B2
(45) Date of Patent: May 29, 2018

(54) FASTENING STRUCTURE FOR BRITTLE-FRACTURABLE PANEL, AND METHOD FOR FASTENING LIGHT TRANSMISSION WINDOW PANEL COMPRISING BRITTLE-FRACTURABLE PANEL EMPLOYING SAME

(71) Applicant: FUJIKIN INCORPORATED, Osaka (JP)

(72) Inventors: Masaaki Nagase, Osaka (JP); Ryousuke Dohi, Osaka (JP); Nobukazu Ikeda, Osaka (JP); Kouji Nishino, Osaka (JP); Michio Yamaji, Osaka (JP); Tadayuki Yakushijin, Osaka (JP)

(73) Assignee: FUJIKIN INCORPORATED, Osaka (JP)

( * ) Notice: Subject to any disclaimer, the term of this patent is extended or adjusted under 35 U.S.C. 154(b) by 106 days.

(21) Appl. No.: 14/889,388

(22) PCT Filed: Apr. 25, 2014

(86) PCT No.: PCT/JP2014/002333
§ 371 (c)(1),
(2) Date: Nov. 5, 2015

(87) PCT Pub. No.: WO2014/181522
PCT Pub. Date: Nov. 13, 2014

(65) Prior Publication Data
US 2016/0084700 A1    Mar. 24, 2016

(30) Foreign Application Priority Data

May 9, 2013    (JP) ................... 2013-099126

(51) Int. Cl.
*G02B 27/02*    (2006.01)
*G01J 1/04*    (2006.01)
(Continued)

(52) U.S. Cl.
CPC .......... *G01J 1/0403* (2013.01); *G01J 1/0407* (2013.01); *G01J 1/42* (2013.01); *G01J 3/0205* (2013.01);
(Continued)

(58) Field of Classification Search
CPC ....... G02B 27/022; G02B 27/028; G01J 1/02; G01J 1/04; G01J 1/0403; G01J 1/42; G01N 2021/058; G01N 21/0303; G01N 21/0307
See application file for complete search history.

(56) References Cited

U.S. PATENT DOCUMENTS 5,671,305 A * 9/1997 Tanaka .................... G02B 6/32
385/33
6,161,875 A    12/2000 Yamaji et al.
(Continued)

FOREIGN PATENT DOCUMENTS

CA    2267453 A    9/1999
CA    2690078 A1    12/2008
(Continued)

OTHER PUBLICATIONS

International Search Report from PCT/JP2014/002333 dated Jul. 22, 2014.

*Primary Examiner* — Bumsuk Won
*Assistant Examiner* — Ephrem Mebrahtu
(74) *Attorney, Agent, or Firm* — Studebaker & Brackett PC (57) ABSTRACT

A fastening structure of a brittle-fracturable panel material includes a first fastening flange, a second fastening flange, and a light transmission window panel made of a brittle-fracturable panel material, wherein the light transmission window panel is nipped between the first fastening flange (Continued)

and the second fastening flange, and both fastening flanges are air-tightly fitted and fastened.

8 Claims, 5 Drawing Sheets

(51) Int. Cl.
    *G01J 1/42*     (2006.01)
    *G02B 1/02*     (2006.01)
    *G01N 21/03*     (2006.01)
    *G01N 21/05*     (2006.01)
    *G02B 7/00*     (2006.01)
    *G01J 5/08*     (2006.01)
    *G01J 3/02*     (2006.01)
    *G01N 21/33*     (2006.01)
    *G01J 5/00*     (2006.01)

(52) U.S. Cl.
    CPC ........ *G01J 5/0875* (2013.01); *G01N 21/0303* (2013.01); *G01N 21/05* (2013.01); *G02B 1/02* (2013.01); *G02B 7/007* (2013.01); *G02B 27/022* (2013.01); *G02B 27/028* (2013.01); *G01J 5/0014* (2013.01); *G01N 21/33* (2013.01)

(56) References Cited

U.S. PATENT DOCUMENTS

| | | | |
|---|---|---|---|
| 2007/0108378 A1* | 5/2007 | Terabayashi | E21B 47/011 250/256 |
| 2010/0127217 A1 | 5/2010 | Lightowlers et al. | |
| 2011/0299067 A1* | 12/2011 | Yokoyama | G01N 21/05 356/213 |

FOREIGN PATENT DOCUMENTS

| | | |
|---|---|---|
| JP | H09-178652 A | 7/1997 |
| JP | H11-280967 A | 10/1999 |
| JP | 2004-108981 A | 4/2004 |
| JP | 2007-305945 A | 11/2007 |
| JP | 3155842 U | 11/2009 |
| JP | 2010-530067 A | 9/2010 |

* cited by examiner

Prior Art

Fig.10

Prior Art

Fig.11

Prior Art

FASTENING STRUCTURE FOR BRITTLE-FRACTURABLE PANEL, AND METHOD FOR FASTENING LIGHT TRANSMISSION WINDOW PANEL COMPRISING BRITTLE-FRACTURABLE PANEL EMPLOYING SAME

FIELD OF THE INVENTION

The present invention relates to an improvement in a fastening structure of a brittle-fracturable panel material made of quartz glass or sapphire or like panel material, and mainly relates to a fastening structure for a brittle-fracturable panel material, and a method for fastening a light transmission window panel comprising a brittle-fracturable panel material employing the same which is used for inline-type photometric analysis process fluid concentration meters or the like used for feedstock fluid supply devices in semiconductor manufacturing devices or the like, which achieves a reduction in size of a sensor portion of concentration meter, allows a light transmission window material to be air-tightly fastened and retained without using any seal material even for process fluids having high deposition property, high photo reactivity, or corrosiveness, and further allows high transparency and high cleanliness in the sensor (particle resistance) to be maintained for a long period of time.

BACKGROUND OF THE INVENTION

Generally, in a feedstock fluid supply device in a semiconductor manufacturing device or the like, it is required to supply a process feedstock fluid with a stable concentration into processing equipment to improve the quality of semiconductor products.

Figure 9:
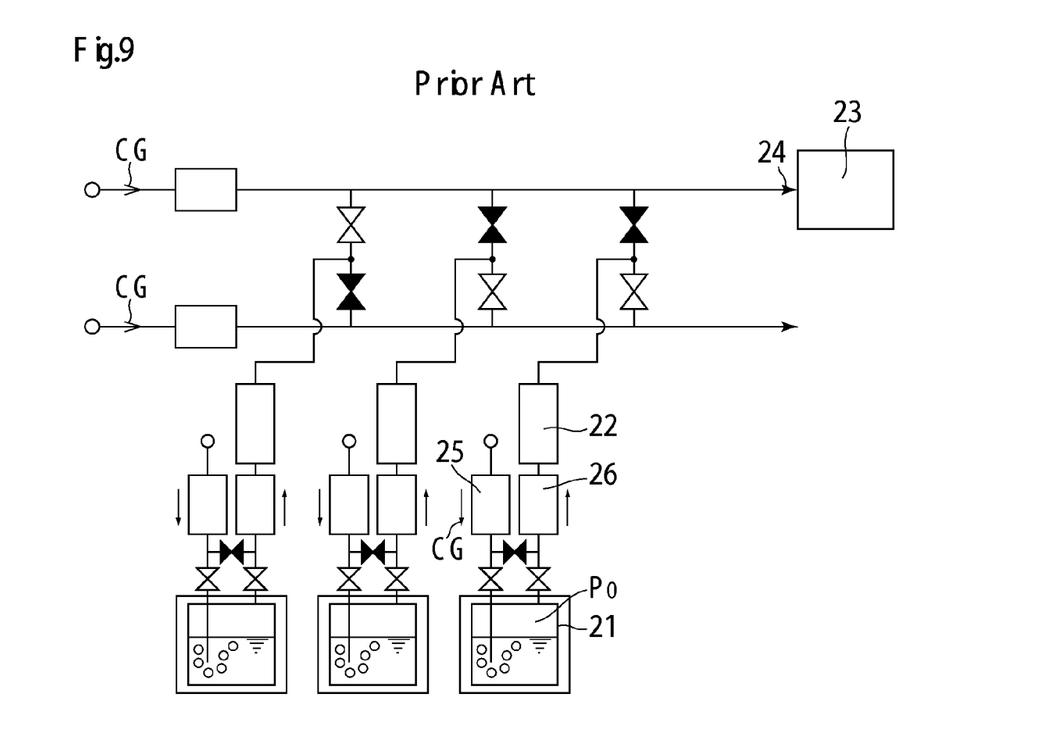
FIG. 9 is a schematic illustrative drawing of a conventional feedstock gas supply device for a semiconductor manufacturing device.

Accordingly, in conventional feedstock fluid supply devices of this type, for example, a bubbling type feedstock fluid supply device as shown in FIG. 9, a photometric analysis type concentration meter 22 is provided in the vicinity of a feedstock vapor outlet of a feedstock tank 21 at a controlled temperature, and the temperature in the feedstock tank 21, the flow rate of a carrier gas CG, the vapor pressure Po in the tank and other conditions are adjusted by a concentration detection signal from the concentration meter 22, whereby a process gas 24 at a predetermined feedstock concentration (for example, process gas containing an organic metallic material vapor such as trimethylgallium TMGa accumulated in the tank 21) is supplied into a reaction furnace 23.

It should be noted that in FIG. 9, reference numeral 25 denotes a thermal massflow controller, and reference numeral 26 denotes a pressure adjustment device for the pressure in the tank.

Figure 10:
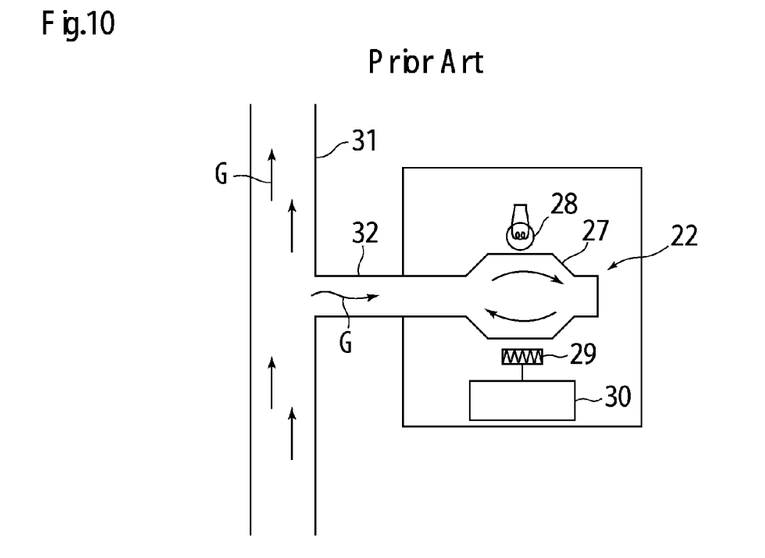
FIG. 10 shows an example of use of a conventional gas concentration meter.
Figure 11:
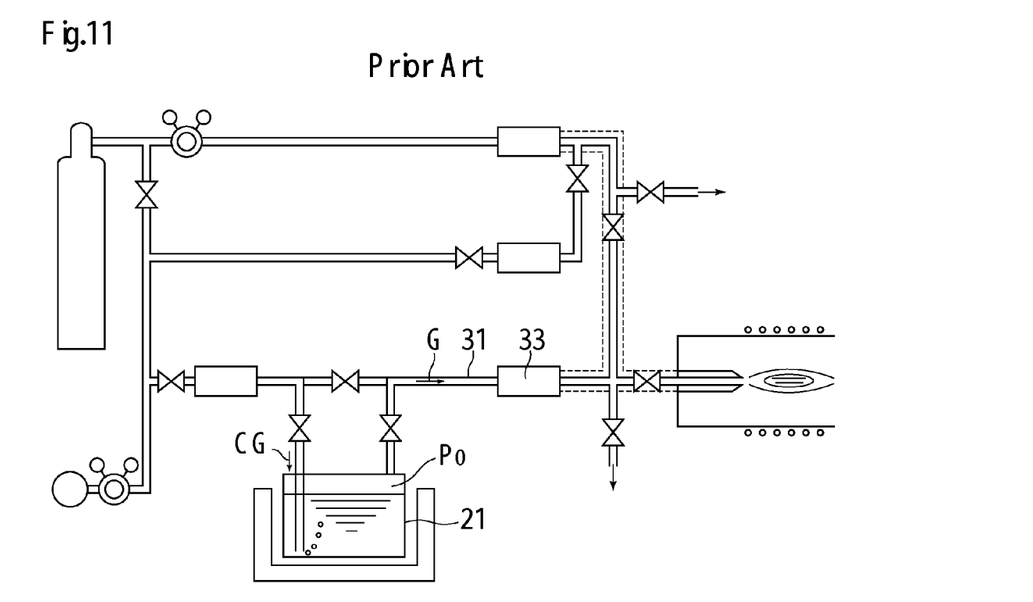
FIG. 11 shows an example of use of another conventional gas concentration meter.

As the concentration meter 22 of the above-mentioned photometric analysis system, the concentration meter 22 with various configurations have been put into practical use, but most of the concentration meter 22 is formed by, as shown in FIG. 10 (Japanese Unexamined Patent Publication No. H9-178652) and FIG. 11 (Japanese Unexamined Patent Publication No. 2004-108981), an optical cell (gas cell) 27, through which a gas G to be measured flows, a light source 28 radiating a light beam into the optical cell 27, a photoreceiver 29 of the light beam passed through the inside of the optical cell 27, an arithmetic unit 30 which determines the absorbance from a signal of the photoreceiver 29 to calculate the concentration of the feedstock, and other components. It should be noted that reference numeral 31 denotes a main pipeline, and reference numeral 32 denotes a branch pipeline.

Such a concentration meter is configured to measure the so-called absorbance of the gas in the optical cell 27 and to calculate the gas concentration by applying the Lambert-Beer law to the measurement results of the absorbance.

In addition, in the latter Japanese Unexamined Patent Publication No. 2004-108981, as shown in FIG. 11, it is so configured that an in-line sensor 33 having an optical cell (absorbance cell) integrated therein is fixed to a pipeline 31, and the photometric measurement of the light passed through the above-mentioned optical cell is performed.

It should be noted that the concentration meter 22 of the above photometric analysis system itself is already known, and their detailed explanation will be omitted herein.

Then, in measuring the concentration of the feedstock gas, first, it is necessary to connect and fasten the optical cell 27 to the pipeline 32 (or pipeline 31), but ensuring airtightness of the connection portion between the optical cell 27 and the pipeline 32 (or pipeline 31) is not easy. For example, it is difficult to fasten the connection with high airtightness in usual screw connection and flange connection by using packing materials or seal materials, and the problem is that it is not easy to obtain the air tightness (external leakage $1\times10^{-10}$ Pa·m$^3$/sec or lower) required in the field of semiconductor manufacturing devices.

Moreover, in order to continuously perform stable gas concentration measurement for a long period of time, various structures forming the optical cell 27, for example, a light transmission window material, need to be firmly fastened and retained onto the main body of the optical cell 27 with high airtightness. Therefore, in the conventional optical cell 27, various types of seal material made of synthetic resins, silver brazing, gold brazing, and the like are used.

Furthermore, in order to perform stable gas concentration measurement continuously, the transparency of the light transmission window material forming the optical cell 27 needs to be maintained stable for a long period of time, and if the transparency changes over time, stable gas concentration measurement becomes difficult.

However, in a conventional gas concentration meter, as mentioned above, in fastening and retaining various types of structures forming the optical cell 27, seal materials made of various types of synthetic resins and silver brazing, gold brazing and other measures are used to ensure air tightness, and thus there is a risk that the seal materials made of synthetic resins, silver brazing, gold brazing and other measures become the source of gases and particles released into organic feedstock material gases. In fact, there is the problem that the purities of the gases are lowered by the discharge of particles. Thus, it is desirable to avoid using silver brazing or gold brazing in the gas supply system for semiconductor manufacturing.

Moreover, since quartz glass is often used as a material of a light transmission window in a conventional gas concentration meter, there is still a problem that, in measuring the concentration of an organic feedstock gas with high corrosiveness or high deposition property, the transparency of the light transmission window is lowered at an early stage due to the corrosion of the window and the deposition of the feedstock, and consequently stable measurement of the concentration of the feedstock gas cannot be performed.

Meanwhile, in place of using the seal materials and the like, the ideas of mechanically fastening various types of structures onto necessary portions directly by nipping have been conceived. However, it is difficult to ensure air tightness by fastening directly or by nipping, and in the case where the member to be fastened is a panel material made of brittle-fracturable material such as quartz glass or sapphire, fastening by mechanical nipping without using any seal material cannot easily provide high sealing property.

As mentioned above, a conventional concentration meter of the photometric analysis system has many problems left to be solved, for example, reducing the size and costs of the facility, ensuring the stability in the accuracy of concentration measurement, maintaining high purity of gas and retaining the air tightness of gas. Therefore, measures for ensuring the sealing property between the light transmission window material and the structure, preventing lowered purity of gas caused by the use of the seal material and preventing lowered transparency of the light transmission window material caused by the corrosiveness of an organic feedstock gas have been urgently sought.

Among them, in particular, providing measures which allow firmly fastening and retaining the light transmission window material forming the major portions of the sensor portion without using any seal material or the like with high air-tightness has been urgently demanded.

CITATION LIST

Patent Literature

Patent document 1: Japanese Unexamined Patent Publication No. H9-178652
Patent document 2: Japanese Unexamined Patent Publication No. 2004-108981
Patent document 3: Japanese Unexamined Patent Publication No. H11-280967

SUMMARY OF THE INVENTION

Technical Problems

In order to solve the problems as stated above of a feedstock concentration meter used in a conventional feedstock fluid supply device and like devices, that are: (I) in the case where a light transmission window material and the like is fastened and retained using a seal material and the like, the purity of the fluid tends to be lowered due to discharged particles from the seal material and discharged gases such as moisture; (II) simplification and reduction in size of the configuration of the concentration meter and reduction in the product costs cannot be easily achieved; (III) stable and highly accurate measurement of the concentration of the feedstock fluid cannot be performed since the transparency of the light transmission window changes; and (IV) it is difficult to increase the airtightness of the connecting part between the optical cell and the pipeline, among other problems. A main object of the present invention is to provide a mechanism which highly air-tightly fastens and retains a brittle-fracturable panel material (light transmission window material) forming the sensor portion without using any seal material, and a method for fastening a light transmission window panel made of a brittle-fracturable panel material using the mechanism, and to thereby provide a process fluid concentration meter of the inline-type photometric system which can handle even an organic feedstock fluid. The meter can be easily inserted and fastened into the fluid passage without leakage, and allows highly accurate and stable concentration measurement. The meter has a small size and allows economic manufacturing.

Solution to Problems

In order to achieve the above object, a first aspect of the fastening structure of the brittle-fracturable panel material according to the present invention is so configured that a light transmission window panel comprising a brittle-fracturable plate material is nipped between a first fastening flange and a second fastening flange, and both fastening flanges are air-tightly fitted and fastened.

A second aspect of the fastening structure of the brittle-fracturable panel material according to the present invention includes:
a first fastening flange having an insertion recessed portion whose inner circumferential surface is contracted stepwise in diameter by a plurality of steps, the stepped portion in the insertion recessed portion serving as a supporting surface for a light transmission window panel made of a brittle-fracturable panel material;
a light transmission window panel made of a brittle-fracturable panel material disposed on the supporting surface of the light transmission window panel, the supporting surface being provided in the insertion recessed portion of the first fastening flange; and
a second fastening flange for nipping the light transmission window panel made of the brittle-fracturable panel material by inserting a protrusion portion having a stepped outer circumferential surface into the insertion recessed portion of the first fastening flange, the protrusion portion being air-tightly fitted and fastened to the insertion recessed portion.

A third aspect of the fastening structure of the brittle-fracturable panel material according to the present invention is such that, in the second aspect mentioned above, the light transmission window panel made of the brittle-fracturable panel material is a sapphire-made light transmission window panel, and the first fastening flange and the second fastening flange are nipped with an applied force of 6 to 12 N.

A fourth aspect of the fastening structure of the brittle-fracturable panel material according to the present invention is such that, in the second aspect mentioned above, the front end face of the protrusion portion of the second fastening flange and a supporting surface of the insertion recessed portion of the first fastening flange form sealing surfaces of the light transmission window panel.

A fifth aspect of the fastening structure of the brittle-fracturable panel material according to the present invention is such that, in the second aspect mentioned above, a gasket accommodating portion is formed on the lower face side of the first fastening flange, and the bottom face of the gasket accommodating portion is a gasket sealing surface.

A sixth aspect of the fastening structure of the brittle-fracturable panel material according to the present invention is such that, in the second aspect mentioned above, an optical fiber insertion hole and a recessed portion for containing photodiode are provided on the second fastening flange.

A method for fastening a light transmission window panel made of the brittle-fracturable panel material according to the present invention includes:
nipping a light transmission window panel made of a brittle-fracturable panel material between a first fastening flange and a second fastening flange; and
fitting and fastening both fastening flanges air-tightly;
providing a recessed portion on a surface of a main body and attaching a gasket type seal into the inside of the recessed portion; then attaching the fitted and fastened fastening flanges into the recessed portion to cause the first fastening flange and the gasket type seal to oppose; further providing a holding/fastening body to enclose the fitted and fastened fastening flanges; and fastening the holding/fastening body to the main body so that the fitted and fastened fastening flanges are air-tightly fastened into the recessed portion via the gasket type seal.

Advantageous Effects of the Invention

In the present invention, a light transmission window panel made of a brittle-fracturable panel material is nipped between a first fastening flange and a second fastening flange, and both fastening flanges are air-tightly fitted and fastened.

Moreover, in the present invention, a fastening structure of a light transmission window panel made of a brittle-fracturable panel material comprises:

a first fastening flange having an insertion recessed portion whose inner circumferential surface is contracted stepwise in diameter by a plurality of steps, the stepped portion in the insertion recessed portion being a supporting surface of a light transmission window panel made of a brittle-fracturable panel material;

a light transmission window panel made of a brittle-fracturable panel material disposed on the supporting surface of the light transmission window panel, the supporting surface being provided in the insertion recessed portion of the first fastening flange; and a second fastening flange for nipping the light transmission window panel made of the brittle-fracturable panel material by inserting a protrusion portion having a stepped outer circumferential surface into the insertion recessed portion of the first fastening flange, the a protrusion portion being air-tightly fitted and fastened to the insertion recessed portion.

As a result, fastening of the light transmission window panel made of the brittle-fracturable panel material can be performed easily and securely, and a required level of tightness can be readily obtained without using any seal material.

Moreover, the light transmission window panel which is the plate material 11 made of a brittle-fracturable material is nipped between the first fastening flange 14 and the second fastening flange 16 and air-tightly fitted and fastened, while both flanges air-tightly fitted and fastened with the light transmission window panel attached thereto are air-tightly inserted into the recessed portion 17 by the holding/fastening body 12 fastened onto the main body 2, so that the light transmission window panel can be easily and firmly retained and fastened with higher air tightness without using any seal material.

In addition, when the light transmission window panel 11 is made of sapphire, the light transmittance is not lowered by even a depositing, reactive, or corrosive fluid, and stable and highly accurate concentration measurement is allowed, while the use of the gasket type seal can eliminate the contamination of impurities into the fluid, compared to a seal structure using other seal materials made of synthetic resins, silver brazing material, gold brazing material and the like.

As mentioned above, the fastening structure for brittle-fracturable panel material according to the present invention and the method for fastening light transmission window panel comprising brittle-fracturable panel material employing the same is highly effective in reducing the size and the cost of equipment, maintaining air tightness, ensuring the stability of the accuracy of concentration measurement and maintaining high purity of gas.

DESCRIPTION OF THE EMBODIMENTS

Embodiments of the present invention will be described below in detail with reference to drawings.

Figure 1:
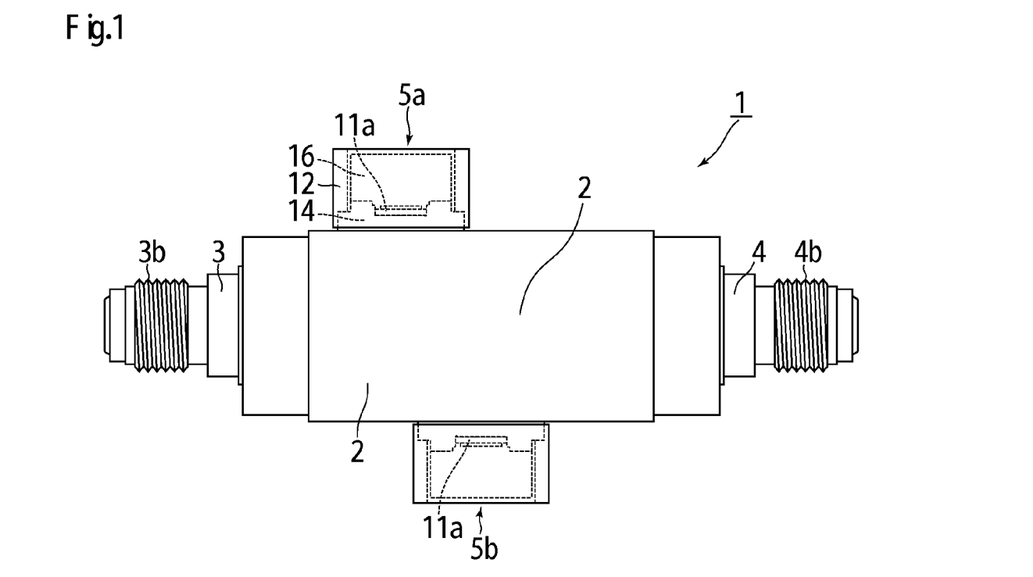
FIG. 1 is a front view of a feedstock fluid concentration detector, to which a fastening structure of a brittle-fracturable panel material according to the present invention is applied.
Figure 2:
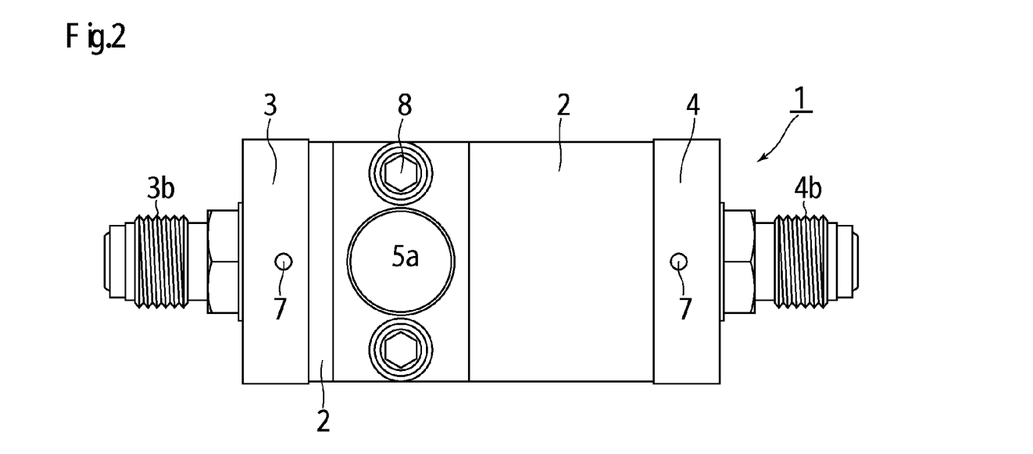
FIG. 2 is a plan view of FIG. 1.
Figure 3:
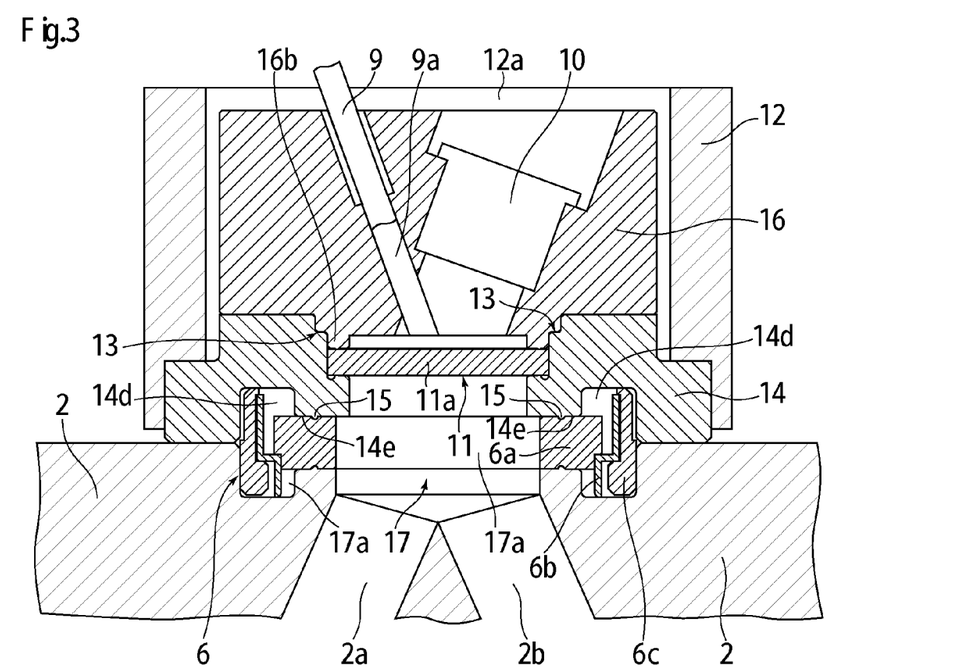
FIG. 3 is a vertical section schematic drawing of a light incident part of a feedstock fluid concentration detector, to which the fastening structure of the brittle-fracturable panel material according to the present invention is applied.
Figure 4:
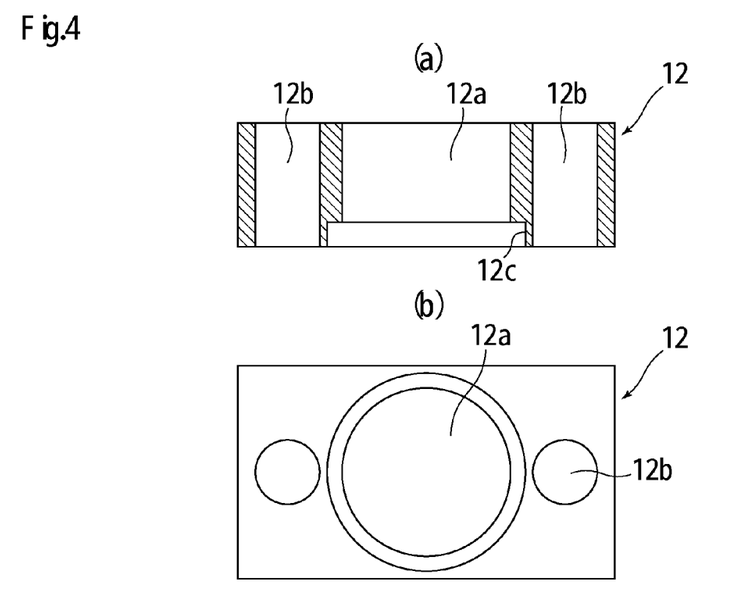
FIG. 4 includes a longitudinal sectional view and plan view of a holding/fastening body of a light incident part shown in FIG. 3.

FIG. 1 is a front view of a feedstock fluid concentration detector to which the fastening structure of a brittle-fracturable panel material according to the present invention is applied; FIG. 2 is a plan view of the same; FIG. 3 is a vertical section schematic drawing of a light incident part of a feedstock fluid concentration detector to which the fastening structure of the brittle-fracturable panel material according to the present invention is applied; and FIG. 4 is a longitudinal sectional view and plan view of a holding/fastening body of the light incident part.

A feedstock fluid concentration detector 1, to which the fastening structure of the brittle-fracturable panel material of the present invention is applied, comprises a detector main body 2 as shown in FIGS. 1 to 4, an inlet block 3 and an outlet block 4 fastened onto both sides of the same, a light incident part 5a provided on the upper face side of the detector main body 2, a photodetector unit 5b provided on the lower face side of the detector main body 2 and other components.

The detector main body 2, inlet block 3 and outlet block 4 mentioned above are formed of material such as stainless steel, and fluid passages 2a, 2b as well as other components are provided therein, respectively. In addition, the inlet block 3 and outlet block 4 are air-tightly fastened to both sides of the detector main body 2 via gasket type seals (not illustrated) with bolts (not illustrated). It should be noted that reference numeral 3b, 4b denote joint portions, reference numeral 7 denotes a leakage inspection hole, and reference numeral 8 denotes a bolt for fastening the light incident part 5a. Furthermore, the photodetector unit 5b and the light incident part 5a are fastened with the bolt for fastening 8 (not illustrated).

The light incident part 5a and photodetector unit 5b mentioned above are provided on the upper face side and lower face side of the detector main body 2, respectively, and a light having a predetermined wavelength in a visible region or an ultraviolet region from a light equipment (not illustrated) composed of light source, diffraction grating, mirror and other components is incident onto a plate material 11 made of a brittle-fracturable material, that is, a light transmission window panel 11a composed of a sapphire-made light transmission window panel, in the light incident part 5a via an optical fiber 9 as shown in FIG. 3.

It should be noted that in FIG. 3, reference numeral 14 denotes a first fastening flange and reference numeral 16 denotes a second fastening flange, and as will be described later, the fastening structure of the brittle-fracturable panel material (light transmission window panel) according to the present invention is configured by both fastening flanges 14, 16.

With reference to FIG. 3, a large part of the incident light is incident onto the fluid passage 2b through the sapphire-made light transmission window panel 11a, but part of the incident light is reflected by the sapphire-made light transmission window panel 11a, and the intensity of this reflected light is detected by a photodiode 10.

The photodetector unit 5b is provided on the lower face side of the detector main body 2 obliquely below the light incident part 5a in a manner of opposing the light incident part 5a, and the light from the light incident part 5a through the fluid passage 2b is incident on a photodiode (not illustrated) in the photodetector unit 5b through the sapphire-made light transmission window panel 11a, and the light intensity of the incident light is detected.

The light intensity detected in the photodetector unit 5b provided on the lower face side varies depending on the concentration and other conditions of the feedstock fluid (processed fluid) flowing through the inside of the fluid passage 2b, and the detected light intensity signal is input into an arithmetic unit (not illustrated), and the feedstock concentration in the feedstock fluid is calculated here.

It should be noted that feedstock concentration C is basically calculated by the following equation (1) based on absorbance A determined by a spectrophotometer.

$$A=\log_{10}(I_0/I)=\varepsilon \times C \times I \tag{1}$$

With the proviso that in equation (1), $I_0$ is the intensity of the incident light from the light incident part 5a, I is the intensity of the transmitted light (the intensity of the incident light into the photodiode 10 of the photodetector unit 5b), $\varepsilon$ is the molar absorptivity of the feedstock, C is the concentration of the feedstock, and A is the absorbance.

The light incident part 5a and the photodetector unit 5b are completely identical in structure, and are formed of, as shown in FIG. 3, a holding/fastening body 12 made of stainless steel having a flange accommodating hole 12a at its center, a first fastening flange 14 provided on the outer surface of the detector main body 2, a second fastening flange 16, the sapphire-made light transmission window panel 11a air-tightly nipped and fastened between both flanges 14, 16, and the photodiode 10 positioned above the light transmission window panel 11a and fastened to the second fastening flange 16, among other components.

The fastening structure of the brittle-fracturable panel material according to the present invention comprises the second fastening flange 16 and first fastening flange 14. As will be described later, the second fastening flange 16 and first fastening flange 14 nip a protrusion portion 16b of the second fastening flange 16 into an insertion recessed portion 14b of the first fastening flange 14 with an applied force of 8 to 12 N, and therefore the front end face of the protrusion portion 16b of the second fastening flange 16 and a supporting surface 14c of the insertion recessed portion 14b of the first fastening flange 14 serve as sealing surfaces for the light transmission window panel 11a to integrate the same air-tightly with the sapphire-made light transmission window panel 11a, which is a brittle-fracturable panel material, being nipped and fastened therebetween.

Thereafter, the second fastening flange 16 and first fastening flange 14 having this sapphire-made light transmission window panel 11a nipped therebetween and integrated therein, are inserted into the flange accommodating hole 12a of the holding/fastening body 12, and then the holding/fastening body 12 is pressed against and fastened to the detector main body 2 by the bolt for fastening 8 with a gasket type seal 6 interposed therebetween, whereby the light incident part 5a and photodetector unit 5b are fastened to the detector main body 2 air-tightly.

It should be noted that in FIG. 3, reference numeral 17 denotes a recessed portion formed on the outer surface of the detector body 2, reference numeral 6a denotes a gasket, reference numeral 13 denotes the sealing surface between fastening flanges 14 and 16, reference numeral 14e denotes the sealing surface between the gasket 6a and the first fastening flange 14, and reference numeral 9a denotes an insertion hole for an optical fiber.

Furthermore, as shown in FIG. 4, the holding/fastening body 12 has the flange accommodating hole 12a provided at the center of a square steel plate with a thickness of 12 to 15 mm, and the insertion hole 12b for the bolt for fastening 8 is provided on both sides of the same. Moreover, at the lower end portion of the holding/fastening body 12, a stepped portion 12c is formed for fitting the upper face of the outer circumference of the first fastening flange 14 and for pressing the same. A lower part of the flange accommodating hole 12a is increased in diameter, and is formed in the accommodating part of the first fastening flange 14.

Next, the fastening structure of the brittle-fracturable panel material (light transmission window panel) of the present invention will be described with reference to FIGS. 5 to 7.

Figure 5:
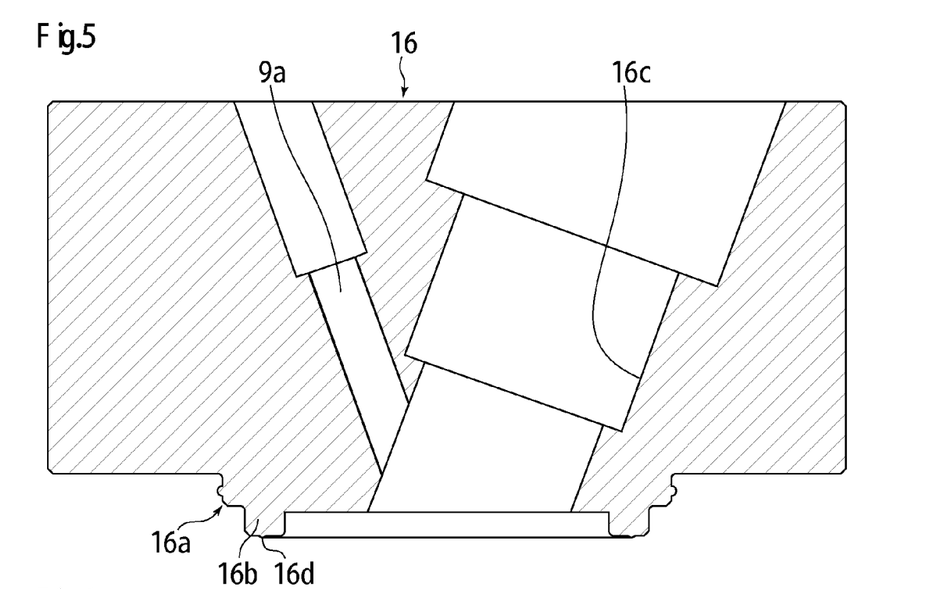
FIG. 5 is a longitudinal sectional view of a second fastening flange according to an embodiment of the present invention.

As shown in FIG. 5, the second fastening flange 16 forming the fastening structure of the brittle-fracturable panel material (light transmission window panel) is formed in the shape of a short cylinder made of stainless steel, and a central portion of its one side (lower face) is formed on the protrusion portion 16b which is contracted in diameter in the form of steps by a two-step stepped portion 16a.

In addition, a front end face 16d of at the front end of the protrusion portion 16b contracted in diameter forms a sealing surface which is in contact with the thin light transmission window panel 11a having a thickness of about 0.8 to 1.5 mm. It should be noted that in FIG. 5, reference numeral 16c denotes a recessed portion for containing photodiode.

Figure 6:
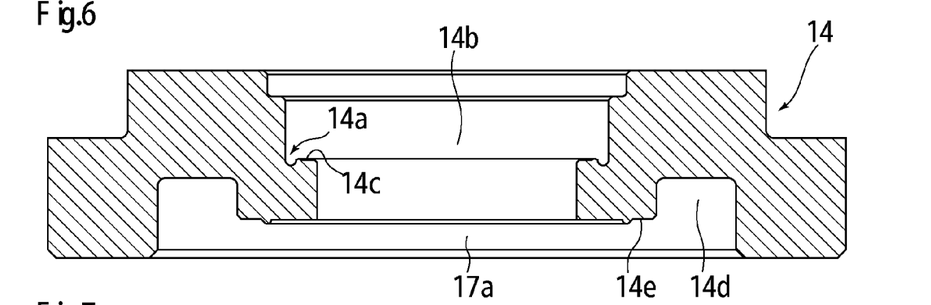
FIG. 6 is a longitudinal sectional view of a first fastening flange according to an embodiment of the present invention.

Meanwhile, the first fastening flange 14 is, as shown in FIG. 6, formed in the shape of a disk of stainless steel, and is formed in the insertion recessed portion 14b contracted in diameter in the form of steps by the stepped portion 14a of a plurality of (herein, three steps) steps at the center of the same. In addition, this insertion recessed portion 14b is formed in the penetration state, and is in communication with a recessed portion 17 of the detector main body 2 (refer to FIG. 3).

Moreover, a middle portion of the above three-step stepped portion 14a forms the accommodating portion of the light transmission window panel 11a, and is mounted and fastened onto the sapphire-made light transmission window panel 11a on the supporting surface 14c which is the stepped portion of its middle potion.

It should be noted that an accommodating portion 14d for the gasket 6a is formed on the lower face side of the first fastening flange 14 and the top half of the gasket type seal 6 is inserted and fastened in there.

The sapphire-made light transmission window panel 11a is mounted on the supporting surface 14c which is the stepped portion of the middle portion of the insertion recessed portion 14b of the first fastening flange 14, then the protrusion portion 16b of the second fastening flange 16 is inserted into the insertion recessed portion 14b, and the second fastening flange 16 is nipped into the first fastening flange 14 with an applied force of 8 to 12 N, so that both fastening flanges 14, 16 are fastened and integrated.

By nipping the flange portion, the pressure contact face between the outer circumferential surface of the protrusion portion 16b and the inner circumferential surface of the insertion recessed portion 14b of both fastening flanges 14, 16, and the front end portion 16d of the projection 16b which is in contact with the outer peripheral edge of the light transmission window panel 11a and the light transmission window supporting face 14c of the insertion recessed portion 14b serve as the sealing surfaces, respectively, which completely prevents the leakage of the fluid in the fluid passage to the outside.

Figure 7:
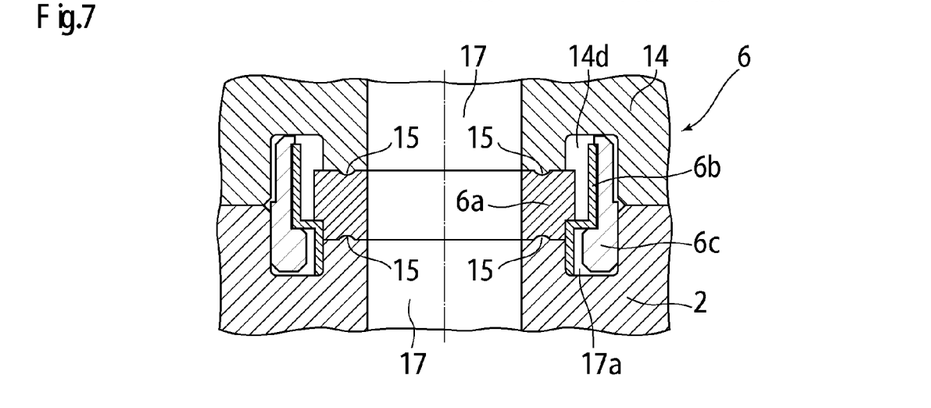
FIG. 7 is a cross-sectional view showing the outline of a gasket type seal of a light incident part to which the fastening structure of the brittle-fracturable panel material of the present invention is applied.

As shown in FIG. 7, the gasket type seal 6 includes the gasket accommodating portion 14d of the first fastening flange 14, a gasket accommodating portion 17a provide on the side of detector main body 2, a ring-shaped gasket 6a, a ring-shaped retainer 6b, a ring-shaped guide ring 6c and other components, and is sealed in duplicate by the sealing surfaces 15, 15.

The sapphire-made light transmission window panel 11a forming the light transmission window made of the plate material 11 made of the brittle-fracturable material is made of a single crystal of so-called high-purity alumina ($Al_2O_3$) having a thickness of 0.8 to 1.5 mm. It is confirmed that the sapphire-made light transmission window panel 11a has excellent wear resistance, corrosion resistance (chemical resistance), heat resistance and other properties, and is used for manufacturing semiconductors without corrosion and modification by organic feedstock gases such that light transparency hardly changes.

Similarly, it has been confirmed that integrating both fastening flanges 14, 16 with a nipping force of 8 to 12 N causes no crack or other damages in the sapphire-made light transmission window panel 11a (outer diameter: 5 to 15 mm).

It should be noted that the above gasket type seal 6, light transmission window panel 11a made of sapphire, photodiode 10 and other components are already known, therefore their detailed explanation will be omitted herein.

Next, the concentration detection test and the results of the feedstock fluid concentration detector 1 according to the present invention will be described below.

Figure 8:
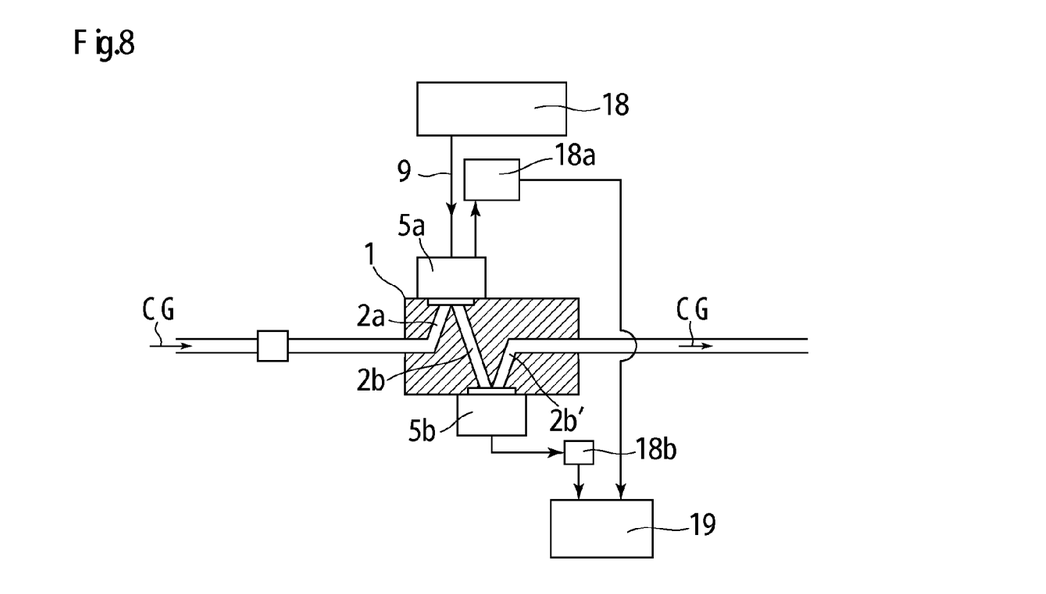
FIG. 8 is a schematic system diagram of a test device of a concentration meter to which the fastening structure of the brittle-fracturable panel material of the present invention is applied.

First, as shown in FIG. 8, the feedstock fluid concentration detector 1 was connected to a supply pipeline of a process gas (organic feedstock TMGa vapor) for semiconductor manufacturing devices in an inline state, and a light was emitted into the light incident part 5a from a light equipment 18 through the optical fiber 9. It should be noted that in the photodiode 10 of the light incident part 5a and the photodetector unit 5b, light receiving surface is selected to be 1.0 mm×1.1 mm in size, 504 mm in diameter, and 3.6 mm in height. Moreover, the sapphire-made light transmission window panel 11a has a thickness of 1.0 mm and a diameter of 8.0 mm. Furthermore, the length of the fluid passage 2b between the light incident part 5a and the photodetector unit 5b is set to be 30 mm, and the inside diameter of the fluid passage is set to be 4.0 mm Φ.

The light is incident on the light incident part 5a, and a detection output from the photodiode 10 of the light incident part 5a is input into an arithmetic unit 19 via a reflected light detection device 18a, and a detection output from the photodiode 10 of the photodetector unit 5b is input into the arithmetic unit 19 via an output light detection device 18b. The concentration of the organic feedstock TMGa vapor circulating in the fluid passage 2a is calculated at predetermined time intervals using equation (1) herein, and the results are recorded and displayed.

The detection output from the reflected light detection device 18a is used for correcting feedstock concentration detection values in the arithmetic unit 19, whereby measurement errors in the feedstock concentration caused by the so-called fluctuation of the incident light from the light equipment 18, the over-time deterioration of the light transmittance of the sapphire-made light transmission window panel 11a and other causes are corrected.

From the results of the test, it has been confirmed that the fastening structure of the brittle-fracturable panel material (sapphire-made light transmission window panel) according to the present invention can ensure a required level of tightness without using any seal materials and allow highly accurate concentration measurement.

INDUSTRIAL APPLICABILITY

The invention of the present application can be used not only for fluid concentration meters of gas supply systems for manufacturing semiconductors, but also for observation windows of fluid concentration meters, pipelines, devices and the like in any fluid supply pipelines handling depositing, photoreactive, or corrosive fluids and devices using such fluids.

REFERENCE SIGNS LIST 1 is a feedstock fluid concentration detector;
2 is a detector main body;
2a is a fluid passage;
2b is a fluid passage;
3 is an inlet block;
3b is a joint portion;
4 is an outlet block;
4b is a joint portion;
5a is a light incident part;
5b is a photodetector unit;
6 is a gasket type seal;
6a is a gasket;
6b is a ring-shaped retainer;
6c is a guide ring;
7 is a leakage inspection hole;
8 is a bolt for fastening;
9 is an optical fiber;

9a is an optical fiber insertion hole;
10 is a photodiode;
11 is a plate material (light transmission window panel) composed of brittle-fracturable material;
11a is a sapphire-made light transmission window panel;
12 is a holding/fastening body;
12a is a flange containing portion;
12b is a bolt insertion hole;
12c is a stepped portion;
13 is a sealing surface;
14 is a first fastening flange;
14a is a step portion;
14b is an insertion recessed portion;
14c is a light transmission window panel supporting surface (sealing surface) of the insertion recessed portion;
14d is a gasket accommodating portion;
16 is a second fastening flange;
16a is a step portion;
16b is a protrusion;
16c is a recessed portion for containing photodiode;
16d is a front end face (sealing surface) of the protrusion;
17 is a recessed portion;
17a is a gasket accommodating portion;
18 is a light equipment;
18a is a reflected light detection device;
18b is an output light detection device;
19 is an arithmetic unit; and
20 is a standard concentration meter;

What is claimed is:

1. A fastening structure of a light transmission window panel made of a brittle-fracturable panel material provided in a concentration meter of a photometric system comprising:
   a first fastening flange having an insertion recessed portion whose inner circumferential surface is contracted stepwise in diameter by a plurality of steps, the stepped portion in the insertion recessed portion serving as a supporting surface for the light transmission window panel;
   the light transmission window panel disposed on the supporting surface for the light transmission window panel, the supporting surface being provided in the insertion recessed portion of the first fastening flange; and
   a second fastening flange having a protrusion portion with a stepped outer circumferential surface for nipping the light transmission window panel, the protrusion portion being inserted into the insertion recessed portion of the first fastening flange, and the protrusion portion being air-tightly fitted and fastened into the insertion recessed portion to form a pressure contact face between the protrusion portion and the insertion recessed portion for sealing, wherein
   the insertion recessed portion of the first fastening flange includes a first recess having a first diameter substantially the same as that of the light transmission window panel and a second recess having a second diameter that is larger than the first diameter,
   the protrusion portion of the second fastening flange includes a first protrusion having a diameter substantially the same as the first diameter and a second protrusion having a diameter substantially the same as the second diameter, and
   an inner circumferential surface of the first recess contacts with an outer circumferential surface of the first protrusion entirely, and an inner circumferential surface of the second recess contacts with an outer circumferential surface of the second protrusion entirely.

2. The fastening structure of the light transmission window panel according to claim 1, wherein the light transmission window panel made of the brittle-fracturable panel material is a sapphire-made light transmission window panel, and wherein the first fastening flange and the second fastening flange are nipped with an applied force of 6 to 12 N.

3. The fastening structure of the light transmission window panel according to claim 1, wherein the front end face of the protrusion portion of the second fastening flange and the supporting surface of the insertion recessed portion of the first fastening flange form sealing surfaces of the light transmission window panel.

4. The fastening structure of the light transmission window panel according to claim 1, wherein a gasket accommodating portion is formed on the lower face side of the first fastening flange, and the bottom face of the gasket accommodating portion forms a gasket sealing surface.

5. The fastening structure of the light transmission window panel according to claim 1, wherein an optical fiber insertion hole and a recessed portion for containing photodiode are provided on the second fastening flange.

6. A method for fastening a light transmission window panel made of a brittle-fracturable panel material in a concentration meter of a photometric system, the method comprising:
   nipping a light transmission window panel made of a brittle-fracturable panel material between a first fastening flange and a second fastening flange, the first fastening flange having an insertion recessed portion, the second fastening flange having a protrusion portion with a stepped outer circumferential surface for nipping the light transmission window panel;
   fitting and fastening both fastening flanges air-tightly such that a pressure contact face is formed between the protrusion portion and the insertion recessed portion for sealing;
   providing a recessed portion on a surface of a main body and attaching a gasket type seal into the inside of the recessed portion; then
   attaching the fitted and fastened fastening flanges into the recessed portion to cause the first fastening flange and the gasket type seal to oppose; further
   providing a holding/fastening body to enclose the fitted and fastened fastening flanges; and
   fastening the holding/fastening body to the body so that the fitted and fastened fastening flanges are air-tightly fastened into the recessed portion via the gasket type seal, wherein
   the insertion recessed portion of the first fastening flange includes a first recess having a first diameter substantially the same as that of the light transmission window panel and a second recess having a second diameter that is larger than the first diameter,
   the protrusion portion of the second fastening flange includes a first protrusion having a diameter substantially the same as the first diameter and a second protrusion having a diameter substantially the same as the second diameter, and
   an inner circumferential surface of the first recess contacts with an outer circumferential surface of the first protrusion entirely, and an inner circumferential surface of the second recess contacts with an outer circumferential surface of the second protrusion entirely.

7. The fastening structure of the light transmission window panel according to claim 1, wherein there are no sealing members between the insertion recessed portion of the first fastening flange and the protrusion portion of the second fastening flange.

8. The fastening structure of the light transmission window panel according to claim 1, wherein the protrusion portion of the second fastening flange is pressed into the insertion recessed portion of the first fastening flange so as to form the pressure contact face between the stepped inner circumferential surface of the insertion recessed portion and the stepped outer circumferential surface of the protrusion portion.

* * * * *